(12) United States Patent
Li et al.

(10) Patent No.: US 10,768,164 B2
(45) Date of Patent: Sep. 8, 2020

(54) METHOD FOR FAST DETECTING PAVEMENT ASPHALT AND EARLY WARNING BASED ON INFRARED SPECTRUM BIG DATA

(71) Applicant: Gansu Province Transportation Planning, Survey & Design Institute Co., Ltd., Lanzhou (CN)

(72) Inventors: Xiaomin Li, Lanzhou (CN); Jingzhuo Zhao, Lanzhou (CN); Dingbang Wei, Lanzhou (CN); Guohong Zhang, Lanzhou (CN); Fukui Zhang, Lanzhou (CN); Qiang Wei, Lanzhou (CN); Hui Wang, Lanzhou (CN); Qingxia Cao, Lanzhou (CN); Min Ding, Lanzhou (CN)

(73) Assignee: Ganzu Province Transportation Planning, Survey & Design Institute Co., Ltd., Lanzhou (CN)

( * ) Notice: Subject to any disclaimer, the term of this patent is extended or adjusted under 35 U.S.C. 154(b) by 0 days.

(21) Appl. No.: 16/175,442

(22) Filed: Oct. 30, 2018

(65) Prior Publication Data

US 2020/0132660 A1 Apr. 30, 2020

(51) Int. Cl.
  *G01N 33/42* (2006.01)
  *G01N 21/35* (2014.01)
  *E01C 23/01* (2006.01)
  *G01N 21/552* (2014.01)

(52) U.S. Cl.
  CPC ............ *G01N 33/42* (2013.01); *E01C 23/01* (2013.01); *G01N 21/35* (2013.01); *G01N 21/552* (2013.01)

(58) Field of Classification Search
  CPC ...... G01N 33/42; G01N 21/35; G01N 21/552; E01C 23/01
  See application file for complete search history.

(56) References Cited

U.S. PATENT DOCUMENTS

2002/0151083 A1* 10/2002 Roussis ............... G01N 33/28
                                                       436/139

* cited by examiner

*Primary Examiner* — Courtney D Thomas
(74) *Attorney, Agent, or Firm* — Mintz Levin Cohn Ferris Glovsky and Popeo, P.C.

(57) ABSTRACT

A method for fast detecting pavement asphalt and early warning based on infrared spectrum data. Infrared spectrum data of standard sample asphalt is collected by adopting an infrared spectrometer, to establish an infrared spectrum database of standard sample asphalt. The infrared spectrum database of the standard sample asphalt and basic asphalt information is introduced into a cloud server through a spectrum input module. A database-matching calculation method and a threshold value is set through a spectrum-matching analysis module. The infrared spectrum data and engineering information of the tested asphalt is collected and uploaded to a cloud platform for storage. A matching calculation between the uploaded data and the spectrograms in the infrared spectrum database of the standard sample asphalt through the cloud server is conducted. An asphalt matching result is outputted to a display terminal. An early-warning message is pushed by the cloud server if a test result is not-match.

13 Claims, 1 Drawing Sheet

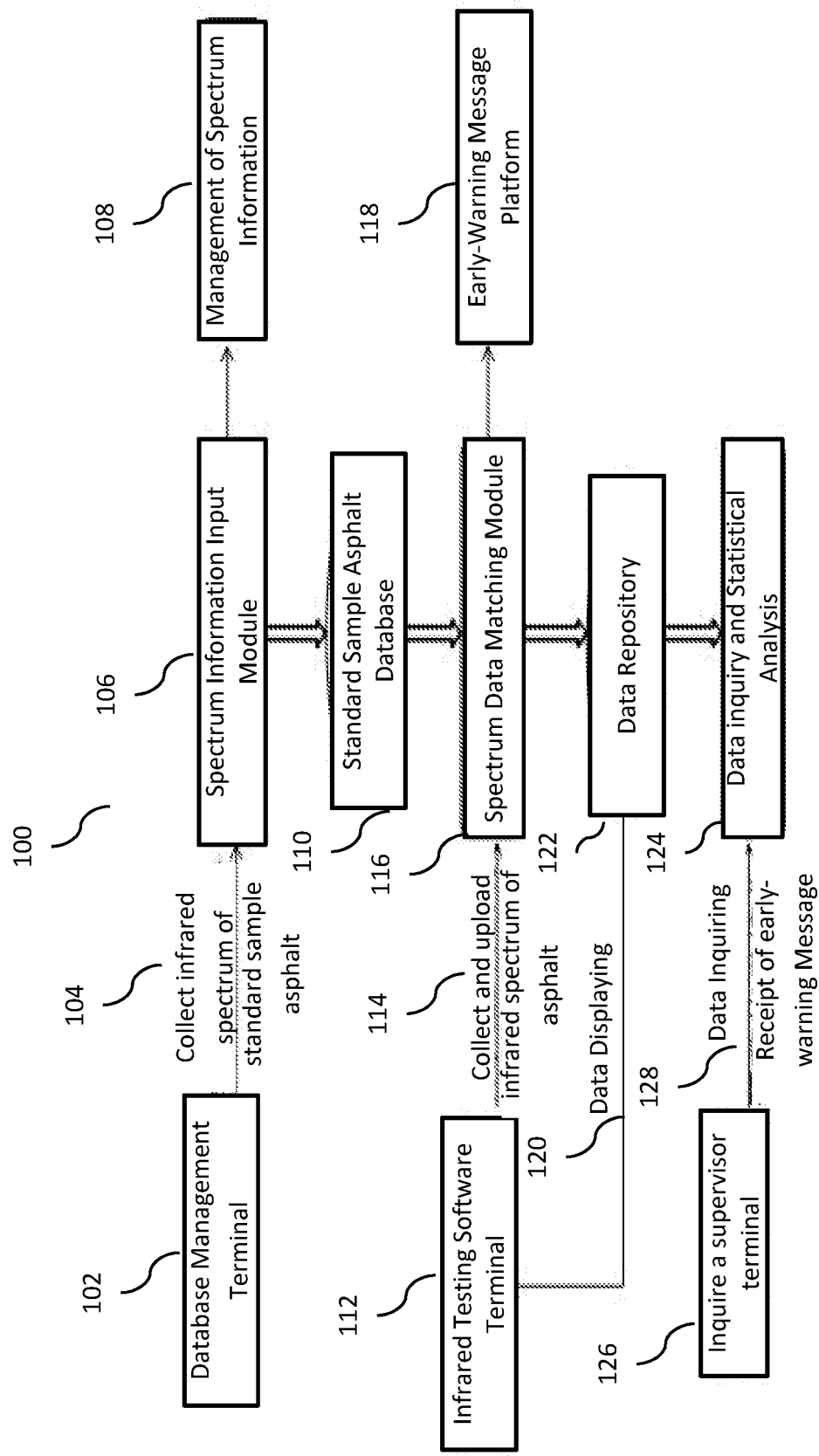

METHOD FOR FAST DETECTING PAVEMENT ASPHALT AND EARLY WARNING BASED ON INFRARED SPECTRUM BIG DATA

TECHNICAL FIELD

The present invention relates to the technical field of methods for detecting the quality stability of pavement petroleum asphalt, and in particular to a method for fast detecting pavement asphalt and early warning based on infrared spectrum big data.

BACKGROUND

Asphalt is a cementing material of asphalt concrete, and the use of petroleum asphalt with stable qualities and excellent performances is the key measure to ensure the service performance and service life of asphalt pavement. More than 55% of China's pavement petroleum asphalt is produced by three companies which are Sinopec Group, China National Petroleum Corporation and China National Offshore Oil Corporation. The oil sources of the asphalt produced by the above companies are stable, but different refineries use different oil sources. For example, the refinery of PetroChina Karamay Petrochemical Company uses Xinjiang heavy oil to produce asphalt, and the refinery of PetroChina Liaohe Petrochemical Company uses Huanxiling heavy oil to produce asphalt. Although the two kinds of asphalt are collectively named asphalt of "Kunlun brand", the difference between qualities of the two kinds of asphalt is large. Karamay asphalt is pavement petroleum asphalt of high quality, but it is difficult to process it and produce modified asphalt due to its composition, while Liaohe asphalt is a good choice for processing into modified asphalt. Meanwhile, the asphalt production of local refineries has been continuously increased in recent years, accounting for about 30% of the asphalt consumption. local refineries use a large number of oil sources, such that the quality of asphalt is very unstable. It is commonplace to sell fakes under the labels of imported asphalt or domestic high-quality asphalt such as asphalt of "Kunlun brand". Therefore, it is extremely necessary to identify the oil sources of asphalt and correspond the same to asphalt refineries, so as to ensure the quality stability of asphalt.

Currently, China uses an asphalt penetration evaluation system to evaluate asphalt through indicators such as penetration, softening points, and ductility before and after asphalt aging. The whole set of indicators takes about 6-8 hours, and is not suitable for the requirement of quickly determining the asphalt quality at a construction site. Meanwhile, the physical index test of asphalt under merely specific conditions and specific loading conditions cannot comprehensively and objectively evaluate the quality of asphalt, resulting in a large difference in pavement performances of asphalt satisfying the same indicators. Moreover, the phenomenon in which other blended and mixed asphalt is used to pretend to be branded asphalt, and troubles such as revelling and pit slots of asphalt pavement caused by asphalt quality problems happens all the time. Therefore, it is extremely necessary to develop a method that can be applied to quickly identify the oil source and refinery of asphalt at the construction site, so as to solve brand faking, blending and mixing problems of asphalt.

SUMMARY

The technical problem to be solved by the present invention is how to provide a method capable of quickly identifying the oil source and refinery of asphalt, monitoring the quality of the asphalt in real time, and ensuring stable composition of the asphalt.

To resolve the above technical problem, the present invention adopts the following technical solution: a method for fast detecting pavement asphalt and early warning based on infrared spectrum big data, including the following steps:

collecting infrared spectrum data of standard sample asphalt by adopting a Fourier infrared spectrometer, to establish an infrared spectrum database of standard sample asphalt;

introducing the infrared spectrum database of the standard sample asphalt and basic asphalt information into a cloud server through a spectrum input module, and setting a database-matching calculation method and a threshold value through a spectrum-matching analysis module;

collecting and uploading the infrared spectrum data and engineering information of the tested asphalt to a cloud platform for storage;

conducting matching calculation between the uploaded data and the spectrograms in the infrared spectrum database of the standard sample asphalt through the cloud server, and outputting an asphalt matching result to a display terminal; and pushing an early-warning message to a supervisor by the cloud server if a test result is not-match.

Further, the Fourier infrared spectrometer uses attenuated total reflection accessories to collect an infrared spectrogram of asphalt, with spectral conditions set as follows: a scanning range of 650 $cm^{-1}$ to 4000 $cm^{-1}$, the number of scanning of 32, and a resolution of 4 $cm^{-1}$.

Further, the specific method for collecting the infrared spectrogram of asphalt by the attenuated total reflection accessory is: firstly scanning the background according to spectrum conditions as set, heating a scraper blade and using the scraper blade to obtain an asphalt sample, uniformly coating the asphalt sample onto the surface of the attenuated total reflection accessory, and collecting and storing the infrared spectrogram of asphalt.

Further, the infrared spectrum database of the standard sample asphalt is established according to the refineries, the standard sample asphalt should be asphalt from a refinery in different years and different production batches, each kind of standard sample asphalt from the refinery is not less than 500, and the year is not less than 3.

Further, the basic asphalt information includes a manufacturer, a production date, a production batch, a sample source, a sampling date, a sample testing date and device information of the asphalt.

Further, there are three calculation methods for database matching of asphalt, which respectively are:

the first calculation method: the cloud server sets the standard peak sensitivity threshold of the infrared spectrum absorption peak of the database as 90, and automatically identifies the locations and number of characteristic absorption peaks of standard sample asphalt, where as a matching condition, if one peak location is different, the asphalt does not match;

the second calculation method: a full spectrum peak area calculation method, where the spectrum matching analysis module of the cloud server performs calculus split calculation on each spectral line in the standard sample asphalt database according to the characteristic absorption peak area selected in the first calculation method, splits the spectral lines in the defined interval into trapezoids for several times, calculates the area of each split trapezoid according to the trapezoid area formula (1), adds up all areas of the trapezoids in this interval to obtain data of each peak area, and calculates the ratio of the peak areas to obtain the data of peak area ratio;

$$S=(a+c) \times h \div 2 \quad (1)$$

in formula 1), S represented an area of a trapezoid, a represented an upper bottom length of the trapezoid, c represented a lower bottom length of the trapezoid, and h represented a height of the trapezoid; aggregation function calculation is performed on data of the peak areas and peak area ratios of characteristic absorption peaks of all spectral curves in the database, to obtain the maximum and minimum values of the peak area and peak area ratio in each interval, and the maximum and minimum values serve as determination threshold of the database, such that when the data of the peak area and peak area ratio for the infrared spectrogram of asphalt is in this range, there is a match, and otherwise, there is no match; and the third calculation method: a full spectrum matching calculation method, where based on implementation of matching in the calculation method 1, the difference between the absorbance values of two spectral lines at the characteristic absorption peak is calculated, and the sum of all the difference values is calculated; the smaller the sum of the difference values between the two spectral lines, the more similar the two spectral lines are; and the formula for calculating the minimum distance between the i-th spectrum in the spectrum database and the tested spectrum $x_k$ is as shown in formula (1):

$$d_i(x_k)=[\Sigma_{j=1}^{n}(x_j-M_j)^2]^{1/2} \quad (2)$$

in formula 2, n represents the number of total characteristic absorption peaks of the spectrum; $x_j$ represents the absorbance value of the j-th absorption peak of the testing spectrum $x_k$; and $M_j$ represents the absorbance value of the j-th absorption peak of the i-th spectrum in the spectrum database; and the distance between the tested spectrum and each spectrum in the spectrum database is calculated one by one, and the spectrum with the smallest distance is selected as the matching result of the tested spectrum.

Further, the engineering information of asphalt includes a project name, a section name, a transport vehicle, a sampling date, a sampling time, an upload time, and device information.

Further, the first method and the third method are used to firstly select a standard sample asphalt database of a refinery, and then determine whether the tested asphalt is the asphalt coming from the refinery.

Further, the first method and the second method are used to conduct spectrogram comparison between the tested asphalt and all asphalt of the database, to select the spectrum in the database with the smallest absorbance difference sum as the matching result of the tested spectrum.

Further, the equipment models of the Fourier infrared spectrometers used for collecting the infrared spectrum of the standard sample asphalt and the tested asphalt are completely the same.

The beneficial effects of adopting the aforementioned technical solution are: the method adopts attenuated total reflection infrared spectrum analysis to establish a standard sample asphalt database, such that the oil source and refinery of asphalt can be determined within 2 min based on large-data comparative analysis, and the source and quality stability of each full truck load of asphalt are monitored in real time during the construction process, which overcomes the problems that the traditional penetration evaluation system is time-consuming and labor-consuming, and meanwhile cannot identify blended, mixed and brand-faked asphalt, and early warns abnormal asphalt in real time, thereby realizing transition from inefficient post inspection to real-time monitoring, and providing reliable and effective data support for a project manager to timely find a problem of the asphalt and make decisions.

BRIEF DESCRIPTION OF THE DRAWINGS

The present invention will be further described in detail with reference to the accompanying drawings and specific embodiments.

FIG. 1 is a flowchart of an exemplary method, according to an embodiment of the present invention.

DETAILED DESCRIPTION

The following describes various technical solutions in the embodiments of the present invention with reference to the accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

In the following description, many specific details are set forth in order to facilitate full understanding of the present invention, but the present invention can also be implemented in other ways other than those described herein. Those skilled in the art can make similar expansion without departing from the connotation of the present invention. Therefore, the present invention is not limited by the specific embodiments disclosed below.

As shown in FIG. 1, an embodiment of the present invention discloses a method 100 for fast detecting pavement asphalt and early warning based on infrared spectrum big data, which is characterized by including the following steps. The method 100 can be performed using one or more of the following components: a database management terminal 102, a spectrum information input module 106, a management of spectrum information component 108, a standard sample asphalt database 110, an infrared testing software terminal 112, a spectrum data matching module 116, an early-warning message platform 118, a data repository 122, an inquire a supervisor terminal 126, and a data inquiry and statistical analysis component 124. One or more of these components can be software, hardware, equipment, and/or any combination thereof. The components can be communicatively coupled using any type of network (including wireless, wired, and/or any combination thereof). As discussed below, one or more of these components can perform collection of infrared spectrum of standard sample asphalt (at 104), collection and uploading of infrared spectrum of asphalt (at 106), and data inquiring and/or receipt of early-warning message (at 108).

It should be noted that, there are two ways to determine the source of asphalt. One is to firstly select a standard sample asphalt database of a refinery and then determine whether the tested asphalt is the asphalt coming from the refinery. The other one is that when no asphalt database of a refinery is selected, spectrogram comparison between the tested asphalt and all asphalt of the database is conducted to select the spectrum in the database with the smallest absorbance difference as the matching result of the tested spectrum.

(1) The infrared spectrum data of the standard sample asphalt is collected by adopting a Fourier infrared spectrometer, to establish an infrared spectrum database of standard sample asphalt.

(2) The infrared spectrum database of the standard sample asphalt and basic asphalt information are introduced into a cloud server through a spectrum input module, and a database-matching calculation method and a threshold value are set through a spectrum-matching analysis module.

(3) The Fourier infrared spectrometer is connected with an infrared spectrum testing software for asphalt, to collect and upload the infrared spectrum data and engineering information of the tested asphalt to a cloud platform for storage.

(4) Matching calculation between the uploaded data and the spectrograms in the infrared spectrum database of the standard sample asphalt is conducted through the cloud server, and the asphalt matching result is output to a display terminal of the testing software.

(5) Matching calculation between the uploaded data and the spectrograms in a specific database of standard sample asphalt is conducted through the cloud server or a computer server, and the output result is of the following three kinds:

1) when a refinery database is selected, the peak appearing position of the absorption peak is exactly the same as that of a standard sample in the standard sample asphalt database, and meanwhile the area and area ratio of the characteristic absorption peak are within a threshold range, then it displays that "the spectrogram of the tested asphalt is consistent with that of the standard sample asphalt in the database";

2) when a refinery database is selected, the peak appearing position of the absorption peak is different from that of a standard sample in the standard sample asphalt database, and meanwhile the area and area ratio of the characteristic absorption peak are not within a threshold range, then it displays that "the tested asphalt is not consistent with the standard sample asphalt in the database"; and 3) when rather than selecting a database, the whole database is used for comparison, then the data of standard sample asphalt in the database having the smallest sum of absorbance difference with the tested asphalt is output as the matching result.

(6) If an asphalt test result is not-match, then after the data matching analysis module of the cloud server obtains the no-match information, a Message API interface of the Aliyun short-message server is called to push an early-warning short message through a Send Message short message of a data center. When the push is successful, the data center receives a Success return message from an Aliyun message API and stores it into the cloud platform. When the push is unsuccessful, the push will be continually conducted, and only the Success return message from the Message API can be received.

(7) database maintenance personnel regularly enrich and improve the standard sample asphalt database, and the data is automatically updated.

Furthermore, the Fourier infrared spectrometer uses attenuated total reflection accessories to collect an infrared spectrogram of asphalt, with spectral conditions set as follows: a scanning range of 650-4000 $cm^{-1}$, the number of scanning of 32, and a resolution of 4 $cm^{-1}$.

The infrared spectrum database of the standard sample asphalt is established according to the refineries, the samples should be samples from different refineries in different years and different production batches, and the standard sample asphalt from each refinery should not be less than 500.

Preferably, the basic asphalt information includes information capable of tracing back to the source of asphalt, such as a manufacturer, a production date, a production batch, a sample source and the like of asphalt.

There are three calculation methods for database matching of asphalt, which respectively are:

calculation method 1: the cloud server sets the standard peak sensitivity threshold of the infrared spectrum absorption peak of the database as 90, and automatically identifies the locations and number of characteristic absorption peaks of standard sample asphalt. As a matching condition, if one peak location is different, the asphalt does not match;

calculation method 2: a full spectrum peak area calculation method, in which the spectrum matching analysis module of the cloud server performs calculus split calculation on each spectral line in the standard sample asphalt database according to the characteristic absorption peak area selected in method 1, splits the spectral lines in the defined interval into trapezoids for several times, calculates the area of each split trapezoid according to the trapezoid area formula as shown in formula 1, adds up all areas of the trapezoids in this interval to obtain data of each peak area, and calculates the ratio of the peak areas to obtain the data of peak area ratio, $$S=(a+c)\times h\div 2 \quad (1)$$

aggregation function calculation is performed on data of the peak areas and peak area ratios of characteristic absorption peaks of all spectral curves in the database, to obtain the maximum and minimum values of the peak area and peak area ratio in each interval, and the maximum and minimum values serve as determination thresholds of the database, such that when the data of the peak area and peak area ratio for the infrared spectrogram of asphalt is in this range, there is a match, and otherwise, there is no match; and calculation method 3: a full spectrum matching calculation method, in which based on implementation of matching in the calculation method 1, the difference between the absorbance values of two spectral lines at the characteristic absorption peak is calculated, and the sum of all the difference values is calculated. The smaller the sum of the difference values between the two spectral lines, the more similar the two spectral lines are. The formula for calculating the minimum distance between the i-th spectrum in the spectrum database and the tested spectrum $x_k$ is as shown in formula (2):

$$d_i(x_k)=[\Sigma_{j=1}^{n}(x_j-M_j)^2]^{1/2} \quad (2)$$

In formula 1, n represents the number of total characteristic absorption peaks of the spectrum; $x_j$ represents the absorbance value of the j-th absorption peak of the testing spectrum $x_k$; and $M_j$ represents the absorbance value of the j-th absorption peak of the i-th spectrum in the spectrum database. The distance between the tested spectrum and each spectrum in the spectrum database is calculated one by one, and the spectrum with the smallest distance is selected as the matching result of the tested spectrum.

Method 3: a full spectrum peak area calculation method, in which the computer executes polymerization function calculation to obtain the maximum and minimum values of the absorption peak area and absorption area ratio at a specific waveband of all asphalt infrared spectrum data in a certain standard sample asphalt database of a refinery, such that if the infrared spectrum data of the tested asphalt is in this range, there is a match, and otherwise there is no match.

Preferably, the engineering information of asphalt includes a project name, a section name, a transport vehicle, a sampling date, a sampling time, an upload time, and device information, etc.

The methods 1 and 3 are used to firstly select a standard sample asphalt database of a refinery, and then determine whether the tested asphalt is the asphalt coming from the refinery. when no asphalt database of a refinery is selected, the methods 1 and 2 are used to conduct spectrogram comparison between the tested asphalt and all asphalt of the database, to select the spectrum in the database with the smallest absorbance difference sum as the matching result of the tested spectrum. The equipment models of the Fourier infrared spectrometers used for collecting the infrared spectrum of the standard sample asphalt and the tested asphalt should be completely the same.

The system used by the aforementioned method includes a Fourier infrared spectrometer, an online infrared spectrum testing software for asphalt, a cloud server and an early-warning platform.

A Fourier infrared spectrometer is equipped with attenuated total reflection accessories, and configured for collecting an infrared spectrogram of asphalt, with spectral conditions set as follows: a scanning range of 650-4000 $cm^{-1}$, the number of scanning of 32, and a resolution of 4 $cm^{-1}$.

The online infrared spectrum testing software for asphalt is installed on a computer, and is connected to the Fourier infrared spectrometer through an USB interface data line, to internally call a device data interface to be responsible for collecting and storing the infrared spectrogram of asphalt. Also, the software uploads infrared spectrogram and engineering information of asphalt to the cloud server through the Internet, and receives and displays the matching result fed back by the cloud server.

The cloud server includes: a spectrum information input module, configured for storing and inputting the spectrum data and information of the standard sample asphalt and storing the spectrum data of the tested asphalt uploaded in real time; and a spectrum matching analysis module, configured for performing matching calculation between the spectrum data of the tested asphalt and the infrared spectrum database of the standard sample asphalt, outputting the matching result to the display terminal of the online testing software, and meanwhile producing a detection record and data statistical information of the asphalt.

The early-warning platform is configured for calling a Message API interface of the Aliyun short-message server to push an early-warning short message through a Send Message short message function of a data center after the data matching analysis module of the cloud server obtains the no-match information if the asphalt testing result is that the database is no matched. When the push is successful, the data center receives a Success return message from a message API of a cloud server and stores it into the cloud platform. When the push is unsuccessful, the push will be continually conducted, and only the Success return message from the Message API can be received.

Embodiment 1

Firstly a standard sample asphalt database of a refinery was selected to determine whether the tested asphalt is the branded asphalt. Specifically, taking asphalt of the refinery of PetroChina Karamay Petrochemical Company as an example, the specific steps were as follows:

(1) 1200 groups of asphalt samples from the Karamay refinery in different years were collected by adopting an attenuated total reflection method through a Fourier infrared spectrometer, and an infrared spectrum database of standard sample asphalt was established.

(2) The infrared spectrum database of the standard sample asphalt and basic asphalt information were introduced into a cloud server, and a database-matching calculation method and a threshold value were set, with the specific setting method being as follows.

(a) The cloud server set the standard peak threshold of the infrared spectrum absorption peak of the database as 90, and the infrared characteristic absorption peaks of standard sample asphalt database of the Karamay refinery was as shown in Table 1 below.

TABLE 1

Matching parameter table of infrared spectrum characteristic absorption peak of asphalt from Karamay refinery.

| | Characteristic Absorption Peak 1 | Characteristic Absorption Peak 2 | Characteristic Absorption Peak 3 | Characteristic Absorption Peak 4 | Characteristic Absorption Peak 5 |
|---|---|---|---|---|---|
| Peak Position $cm^{-1}$ | 2920 ± 5 | 2850 ± 5 | 2725 ± 5 | 1705 ± 5 | 1600 ± 5 |
| | Characteristic Absorption Peak 6 | Characteristic Absorption Peak 7 | Characteristic Absorption Peak 8 | Characteristic Absorption Peak 9 | Characteristic Absorption Peak 10 |
| Peak Position $cm^{-1}$ | 1455 ± 5 | 1375 ± 5 | 1305 ± 5 | 1165 ± 5 $cm^{-1}$ | 1032.65 |
| | Characteristic Absorption Peak 11 | Characteristic Absorption Peak 12 | Characteristic Absorption Peak 13 | Characteristic Absorption Peak 14 | Characteristic Absorption Peak 15 |
| Peak Position $cm^{-1}$ | 965 ± 5 | 870 ± 5 | 812 ± 5 | 745 ± 5 | 720 |

(b) The analysis module of the cloud server performed calculus split calculation on each spectral line in the database of the Karamay refinery according to the areas of the aforementioned 15 characteristic absorption peaks selected in (1), split the spectral lines in the defined interval into trapezoids for several times, calculated the area of each split trapezoid according to the trapezoid area formula as shown in formula 2, added up all areas of the trapezoids in this interval to obtain data of each peak area, and calculated the ratio of the peak areas to obtain the data of peak area ratio, $$S=(a+c)\times h\div 2 \qquad (1)$$

S represented an area of a trapezoid, a represented an upper bottom length of the trapezoid, c represented a lower bottom length of the trapezoid, and h represented a height of the trapezoid; aggregation function calculation was performed on data of the peak areas and peak area ratios of characteristic absorption peaks of all spectral curves in the asphalt database of the Karamay refinery, to obtain the maximum and minimum values of the peak area and peak area ratio in each interval, and the maximum and minimum values served as determination thresholds of the database, such that when the data of the peak area and peak area ratio for the infrared spectrogram of asphalt was in this range, there was a match, and otherwise, there was no match.

(3) The Fourier infrared spectrometer is connected with an infrared spectrum testing software for asphalt, to collect and upload the infrared spectrum data and engineering information of the tested asphalt to a cloud platform for storage.

(4) Matching calculation between the uploaded data and the standard samples in the asphalt database of the Karamay refinery, was conducted through the cloud server or a computer server, and the asphalt matching result was output to a display terminal of the testing software. The output results were of two kinds:

(a) when the peak appearing position of the absorption peak was exactly the same as that of a standard sample in the asphalt database of the Karamay refinery, and meanwhile the area and area ratio of the characteristic absorption peak were within a threshold range, then it displayed that "the spectrogram of the tested asphalt is consistent with that of the standard sample asphalt in the database"; and (b) when the peak appearing position of the absorption peak was different from that of a standard sample in the asphalt database, and meanwhile the area and area ratio of the characteristic absorption peak were not within a threshold range, then it displayed that "the tested asphalt is not consistent with the standard sample asphalt in the database".

(5) If an asphalt test result is not-match, then after the data matching analysis module of the cloud server obtains the no-match information, a Message API interface of the Aliyun short-message server is called to push an early-warning short message through a Send Message short message of a data center. When the push is successful, the data center receives a Success return message from an Aliyun message API and stores it into the cloud platform. When the push is unsuccessful, the push will be continually conducted, and only the Success return message from the Message API can be received.

Embodiment 2

When no asphalt database of a refinery was selected, spectrogram comparison between the tested asphalt and all asphalt of the database was conducted to select the spectrum in the database with the smallest distance as the matching result of the tested spectrum, with the specific steps being as follows:

(1) The infrared spectrum data of the standard sample asphalt was collected by adopting a Fourier infrared spectrometer, to establish an infrared spectrum database of standard sample asphalt.

(2) The infrared spectrum database of the standard sample asphalt and basic asphalt information were introduced into a cloud server through a spectrum input module, and a database-matching calculation method and a threshold value were set through a spectrum-matching analysis module.

(3) The Fourier infrared spectrometer was connected with an infrared spectrum testing software for asphalt, to collect and upload the infrared spectrum data and engineering information of the tested asphalt to a cloud platform for storage.

(4) Matching calculation between the uploaded data and all of the spectrograms in the infrared spectrum database of the standard sample asphalt was conducted through the cloud server, and the data of standard sample asphalt in the database having the smallest sum of absorbance difference with the tested asphalt was output as the matching result.

(5) If an asphalt testing result is not-match, then after the data matching analysis module of the cloud server obtained the no-match information, a Message API interface of the Aliyun short-message server was called to push an early-warning short message through a Send Message short message of a data center. When the push is successful, the data center receives a Success return message from an Aliyun message API and stores it into the cloud platform. When the push is unsuccessful, the push will be continually conducted, and only the Success return message from the Message API can be received.

(6) Database maintenance personnel regularly enrich and improve the standard sample asphalt database, and the data is automatically updated.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively and/or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input (e.g., push/touch button, etc.). Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few implementations have been described in detail above, other modifications or additions are possible. In particular, further features and/or implementations can be provided in addition to those set forth herein. For example, the implementations described above can be directed to various combinations and subcombinations of the disclosed features and/or combinations and subcombinations of several further features disclosed above. In addition, the logic flows depicted in the accompanying FIGURES and/or described herein do not necessarily require the particular order shown, or sequential order, to achieve desirable results. Other implementations may be within the scope of the following claims.

What is claimed is:

1. A method for fast detecting a source of a pavement asphalt sample, the method comprising:
   collecting, using a Fourier infrared spectrometer, an infrared spectrum data of the asphalt sample;
   providing, using at least one processor, the collected infrared spectrum data of the asphalt sample to a cloud server, the at least one processor being communicatively coupled to the Fourier infrared spectrometer and the cloud server;
   receiving and storing, using a spectrum input module of the cloud server, the collected infrared spectrum data of the asphalt sample at the cloud server;
   selecting, using a spectrum-matching analysis module of the cloud server, a database-matching calculation method to be executed by the cloud server and a standard peak sensitivity threshold value for detecting the source of the asphalt sample;
   querying, using the cloud server, spectrogram asphalt sample data stored in an infrared spectrum database based on the selected standard peak sensitivity threshold value, the infrared spectrum database being communicatively coupled with the cloud server;
   comparing, by the cloud server executing the selected database-matching calculation method, the collected infrared spectrum data and the spectrogram asphalt sample data stored in the infrared spectrum database;
   displaying, based on the comparing and upon determination of a match between the collected infrared spectrum data and one or more spectrogram asphalt sample data, an identification of the source of the collected asphalt sample on a display terminal; and
   transmitting, by the cloud server, based on the comparing and upon determination of an absence of a match between the collected infrared spectrum data and one or more spectrogram asphalt sample data, an early-warning message to the display terminal.

2. The method according to claim 1, wherein the Fourier infrared spectrometer uses one or more attenuated total reflection accessories, to collect the infrared spectrum data, having at least one of the following spectral conditions: a scanning range of 650 $cm^{-1}$ to 4000 $cm^{-1}$, 32 scans, a resolution of 4 $cm^{-1}$, and any combination thereof.

3. The method according to claim 2, wherein the collecting further comprises
   collecting, using the one or more attenuated total reflection accessories, the infrared spectrum data by
     scanning a background, using one or more of the spectral conditions,
     heating a scraper blade and using the scraper blade to obtain the asphalt sample,
     uniformly coating the asphalt sample onto a surface of the one or more attenuated total reflection accessories, and
     collecting and storing the infrared spectrum data.

4. The method according to claim 1, wherein the infrared spectrum database is generated using the spectrogram asphalt sample data received from one or more, wherein the spectrogram asphalt sample data is associated with asphalt samples that include at least one of the following: asphalt samples produced a refinery as obtained at different periods of time, asphalt samples obtained from different production batches produced by the refinery, different types of asphalt samples produced by the refinery, different number of asphalt samples produced by the refinery, and any combination thereof.

5. The method according to claim 1, further comprising receiving and storing, using a spectrum input module of the cloud server, a basic asphalt information associated with the asphalt sample at the cloud server, wherein the basic asphalt information includes at least one of the following: a manufacturer data, a production date, a production batch data, a sample source data, a sampling date, a sample testing date, device information of the asphalt, and any combination thereof.

6. The method according to claim 1, wherein the database-matching calculation method includes at least one of the following:
a first calculation method, whereby the cloud server is configured to
set the standard peak sensitivity threshold value of an infrared spectrum absorption peak associated with spectrogram asphalt sample data stored in the infrared spectrum database at 90, and
automatically identify one or more locations and number of characteristic absorption peaks of standard asphalt samples, wherein as a matching condition, if one peak location is different, the collected infrared spectrum data of the asphalt sample does not match to any data stored in the infrared spectrum database;
a second or a full spectrum peak area calculation method, wherein the spectrum matching analysis module of the cloud server is configured to
perform calculus split calculation on each spectral line in the data stored in the infrared spectrum database according to the characteristic absorption peak area set in the first calculation method,
split the spectral lines in one or more defined intervals into trapezoids several times,
calculate an area of each split trapezoid according to the trapezoid area S,
add up all areas of the trapezoids in the one or more intervals to determine data of each peak area, and
calculate a ratio of the peak areas to determine a data of peak area ratio, as follows $$S=(a+c)\times h\div 2$$

wherein S represents an area of a trapezoid, a represents an upper bottom length of the trapezoid, c represents a lower bottom length of the trapezoid, and h represents a height of the trapezoid;
wherein an aggregation function calculation is performed on data of the peak areas and peak area ratios of characteristic absorption peaks of all spectral curves in the infrared spectrum database, to obtain the maximum and minimum values of the peak area and peak area ratio in each interval, and the maximum and minimum values serve as a determination threshold of the infrared spectrum database, such that when the data of the peak area and peak area ratio for the infrared spectrogram of the collected asphalt sample is in a range between the maximum and the minimum values, the collected infrared spectrum data of the asphalt sample matches data stored in the infrared spectrum database, and otherwise, there is no match; and
a third or a full spectrum matching calculation method, wherein the cloud server is configured to
calculate, using the first calculation method, a difference between one or more absorbance values of two spectral lines at the characteristic absorption peak,
calculate a sum of all the difference values;
wherein the smaller the sum of the difference values between the two spectral lines, the more similar the two spectral lines are; and
wherein a minimum distance between the i-th spectrum in the infrared spectrum database and the tested spectrum $x_k$ is determined as follows:

$$d_i(x_k)=[\Sigma_{j=1}{}^n(x_j-M_j)^2]^{1/2}$$

wherein n represents the number of total characteristic absorption peaks of the spectrum; $x_j$ represents the absorbance value of the j-th absorption peak of the testing spectrum $x_k$; and $M_j$ represents the absorbance value of the j-th absorption peak of the i-th spectrum in the spectrum database; and the distance between the tested spectrum and each spectrum in the spectrum database is calculated one by one, and the spectrum with the smallest distance is selected as the matching result of the tested spectrum.

7. The method according to claim 1, further comprising receiving and storing, using a spectrum input module of the cloud server, an engineering information associated with the asphalt sample at the cloud server, wherein the engineering information of asphalt comprises at least one of the following: a project name, a section name, a transport vehicle, a sampling date, a sampling time, an upload time, device information, and any combination thereof.

8. The method according to claim 6, wherein the first calculation method and the third calculation method are executed by the cloud server to select a spectrogram asphalt sample data stored in the infrared spectrum database of a refinery, and then determine whether the collected asphalt is produced by the refinery.

9. The method according to claim 6, wherein the first calculation method and the second calculation method are executed by the cloud server to
conduct a spectrogram comparison between the collected asphalt and data stored in the infrared spectrum database,
select a spectrum data stored in the infrared spectrum database with the smallest absorbance difference sum as the matching result of the collected infrared spectrum data.

10. The method according to claim 1, wherein the collecting is performed using a plurality of Fourier infrared spectrometers the same equipment models.

11. The method according to claim 4, wherein the number of asphalt samples produced by the refinery is not less than 500, and a number of the periods of time is not less than 3.

12. A system for fast detecting a source of a pavement asphalt sample, the system comprising:
at least one programmable processor; and
a non-transitory machine-readable medium storing instructions that, when executed by the at least one programmable processor, cause the at least one programmable processor to perform operations comprising:
collecting an infrared spectrum data of the asphalt sample;

receiving and storing, using a spectrum input module, the collected infrared spectrum data of the asphalt sample at the cloud server;

selecting, using a spectrum-matching analysis module, a database-matching calculation method for execution and a standard peak sensitivity threshold value for detecting the source of the asphalt sample;

querying, using the cloud server, spectrogram asphalt sample data stored in an infrared spectrum database based on the selected standard peak sensitivity threshold value, the infrared spectrum database being communicatively coupled with the cloud server;

comparing, by executing the selected database-matching calculation method, the collected infrared spectrum data and the spectrogram asphalt sample data stored in the infrared spectrum database;

displaying, based on the comparing and upon determination of a match between the collected infrared spectrum data and one or more spectrogram asphalt sample data, an identification of the source of the collected asphalt sample on a display terminal; and transmitting, based on the comparing and upon determination of an absence of a match between the collected infrared spectrum data and one or more spectrogram asphalt sample data, an early-warning message to the display terminal.

13. A computer program product for fast detecting a source of a pavement asphalt sample, the computer program product comprising a non-transitory machine-readable medium storing instructions that, when executed by at least one programmable processor, cause the at least one programmable processor to perform operations comprising:

collecting an infrared spectrum data of the asphalt sample;

receiving and storing, using a spectrum input module, the collected infrared spectrum data of the asphalt sample at the cloud server;

selecting, using a spectrum-matching analysis module, a database-matching calculation method for execution and a standard peak sensitivity threshold value for detecting the source of the asphalt sample;

querying, using the cloud server, spectrogram asphalt sample data stored in an infrared spectrum database based on the selected standard peak sensitivity threshold value, the infrared spectrum database being communicatively coupled with the cloud server;

comparing, by executing the selected database-matching calculation method, the collected infrared spectrum data and the spectrogram asphalt sample data stored in the infrared spectrum database;

displaying, based on the comparing and upon determination of a match between the collected infrared spectrum data and one or more spectrogram asphalt sample data, an identification of the source of the collected asphalt sample on a display terminal; and transmitting, based on the comparing and upon determination of an absence of a match between the collected infrared spectrum data and one or more spectrogram asphalt sample data, an early-warning message to the display terminal.

* * * * *